United States Patent [19]

Crane et al.

[11] Patent Number: 5,149,646
[45] Date of Patent: Sep. 22, 1992

[54] PROCESS FOR ISOLATING GALACTOSE OXIDASE

[75] Inventors: Laura J. Crane, Buttzville, N.J.; Adam W. Mazur, Cincinnati, Ohio; David R. Nau, Lebanon, N.J.; Bernard W. Kluesener, Harrison, Ohio

[73] Assignee: The Procter & Gamble Company, Cincinnati, Ohio

[21] Appl. No.: 807,010

[22] Filed: Dec. 13, 1991

Related U.S. Application Data

[63] Continuation-in-part of Ser. No. 453,729, Dec. 20, 1989, abandoned.

[51] Int. Cl.$^5$ .............................................. C12N 9/04
[52] U.S. Cl. ..................................... 435/190; 435/911
[58] Field of Search ......................................... 435/190

[56] References Cited

U.S. PATENT DOCUMENTS

| | | | |
|---|---|---|---|
| 4,640,909 | 2/1987 | Ramsden et al. | 502/407 |
| 4,661,248 | 4/1987 | Ramsden et al. | 210/198 |
| 4,721,573 | 1/1988 | Ramsden et al. | 210/635 |

OTHER PUBLICATIONS

Tressel et al., Methods in Enzymology, 89, pp. 163-171 (1982).
G. Reed et al., Prescott & Dunn's Industrial Microbiology, Separation Methods, pp. 654-657 (AVI Publishing, 4th Ed.).
Gelman Sciences, The Filter Book, Laboratory Filtration, p. 13 (1991).
Scopes, Protein Purification, Second Edition (Springer-Verlag), pp. 94-99, 104-109.
Biochim. Biophys. Acta, 544, 163-169 (1978).
Analytical Biochem., 105, 150-153 (1980).
Appl. Microbiol, 13, (5) 686-693 (1965).
Agric. Bio. Chem. 45, (10) 2311-2316 (1981).
Israel J. Chem., 3, 193 (1966).

Primary Examiner—Douglas W. Robinson
Assistant Examiner—S. Saucier
Attorney, Agent, or Firm—Rose Ann Dabek; Jerry J. Yetter

[57] ABSTRACT

A method of isolating and purifying galactose oxidase from a fungus media is disclosed. The supernatant liquid from the fermentation broth is subjected to ultrafiltration and then separated on a carboxy-sulfon cation exchange column using high performance liquid chromatography. Copper ions must be present to insure enzyme activity.

12 Claims, No Drawings

PROCESS FOR ISOLATING GALACTOSE OXIDASE

This is a continuation-in-part of application Ser. No. 07/453,729 filed Dec. 20, 1989, now abandoned.

FIELD OF THE INVENTION

A method of isolating and purifying galactose oxidase from a fungus media is disclosed. The supernatant liquid from a fermentation broth is subjected to ultrafiltration and then separated on a carboxy sulfon cation exchange column using high performance liquid chromatography (HPLC). Copper ions must be present to insure enzyme activity.

BACKGROUND OF THE INVENTION

Galactose oxidase (E.C. 1.1.3.9, GOase) is a copper-containing extracellular enzyme which oxidizes the primary hydroxyl groups of many alcohols and of galactose. Although the enzyme is produced by a number of fungus species, fermentation of *Dactylium dendroides* is currently the best practical source. A simple method for the growth of this fungus and purification of the excreted enzyme from the growth medium is described by Tressel and Kosman, *Analytical Biochemistry*, 105. 150-153 (1930).

In this process the enzyme is grown in a fungal culture aerobically in the dark for several days at 20° C. This fungus is then transferred to a glucose-based liquid medium and grown aerobically for about 2 days at 20° C. A completely artificial medium is used; it is a mixture of sorbose, glucose, traces of metal ions as micronutrients, and thiamine as the necessary vitamin. Growth of the culture takes usually 5 to 7 days. Isolation of the galactose oxidase involves a number of steps which begins with precipitation in the presence of microcrystalline cellulose. The purification is completed by chromatography on a phosphocellulose column.

The enzyme contains 1 atom of copper and the presence of the cupric ($Cu^{+2}$ ions is necessary for enzymic activity. When the galactose oxidase is grown under conditions of copper deprivation, *Dactylium dendroides* synthesizes and excretes a catalytically inactive protein, aplagalactose oxidase. Catalytic activity of the protein appears when cupric ion is added to the copper depleted solution (see, Shatzman and Kosman, *Biochim. Biophys. Acata.* 1978, 544, 163-169 and Markus et al., *G. Avigad. Appl.. Microbiol.*, 13 (5), 686-693 (1965)). This result implies that although copper is necessary for the catalytic activity of galactose oxidase, cupric ion neither induces synthesis nor is necessary for the complete assembly and secretion of proteins by *Dactylium dendroides*. On the other hand, Japanese workers (Aisaka and Terada, Agric. Bio. Chems., 45, 2311-2316 (1981)) concluded that the synthesis of galactose oxidase protein by *Gibberella Fujikuroi* is a phenomenon regulated by copper.

Copper ion also preserves enzyme activity in unpurified fermentation medium by preventing complexation of galactose oxidase with an inhibitor (Avigad and Markus, *Israel J. Chem.*, 3, 193 (1966)). It is known that *Dactylium dendroides* produces at least one galactose oxidase inhibitor identified as a heptapeptide. This protein forms a stable inactive complex with galactose oxidase in the absence of copper. Presence of 1 to 10 mM cupric ion not only prevents this inhibition but also causes slow activation of the inhibited enzyme. The inhibiting components are usually removed from galactose oxidase preparations by chromatography.

The present process produces about a 45% yield of enzyme (measured as recovered activity) over a three day isolation period. It has now been found that this isolation and purification can be simplified and conducted on large quantities of enzyme preparation mixtures by the use of ultrafiltration and high performance liquid chromatography purification techniques. Gram quantities of the galactose oxidase can be prepared in a day.

Accordingly, it is an object of this invention to prepare large quantities of galactose oxidase in yields of above 70% (measured as recovered total activity) in an efficient manner.

All percentages are by weight unless otherwise indicated.

SUMMARY OF INVENTION

A process for preparing and isolating pure galactose oxidase is disclosed. The process comprises the steps of
(1) aerobically fermenting *Dactylium dendroides* in a medium comprising a nitrogen source, a carbon source and trace metals and thiamine at a temperature of between 20 .C to about 25° C.;
(2) filtering the supernatant liquid from the fermentation broth using a 0.15 to 0.25 μm filter;
(3) concentrating the enzyme by ultrafiltration with a 10, 000 molecular weight membrane;
(4) equilibrating the retentate from (3) with a buffer containing copper ions and histidine;
(5) optionally, treating the retentate with DEAE cellulose to remove contaminating proteins;
(6) purifying the enzyme on a carboxy-sulfon column using high pressure or high performance liquid chromatography methods.

DETAILED DESCRIPTION OF THE INVENTION

A. Fermentation

A starter broth of *Dactylium dendroides* or other fungal source of galactose oxidase is prepared. The procedure of Kosman, ibid involves preparation of stationary dextrose agar slants which are inoculated with *Dactylium dendroides*. The inoculated slants are grown aerobically in the dark for approximately two days at about 20° C. to form a uniformly white, fluffy coating of fungus. Lengthy exposure to sunlight or an excessively warm incubation temperature results in "abnormal" cultures which are discolored and finely matted.

A small portion of this starter fungus is mixed with a liquid medium to grow the galactose oxidase. This completely artificial medium contains sorbose or glucose as the carbon sources, traces of metal ions as micronutrients and thiamine as the necessary vitamin. Growth in the culture takes 5 to 7 days. The pH of the growth media is neutral.

Copper sulfate (from 10 μm to about 60 μm) increases the enzyme activity in the fermentation medium and improves reproducibility of the fermentation runs as compared to batches fermented by the standard method where the copper sulfate concentration was 11 μM. On the other hand, when the ($Cu^{2+}$) cupric concentration was increased to 1 mM, growth of mycelia was clearly retarded and only traces of galactose oxidase activity were detected.

The usual batch size for growing the *Dactylium Dendroides* is in 20 (L)liter containers. This process can easily be scaled up to grow the fungus in kiloliter containers. Table 1 provides a flow chart for the preparation of the enzyme broth in 250L fermentor.

TABLE 1

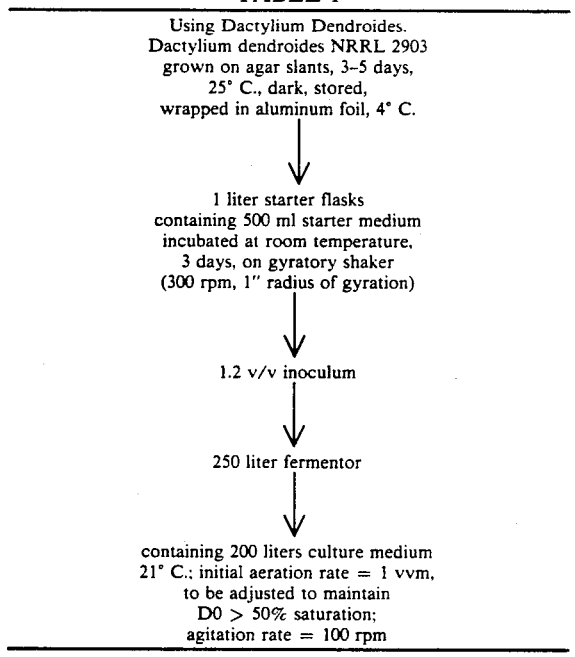

Using Dactylium Dendroides.
Dactylium dendroides NRRL 2903 grown on agar slants, 3-5 days, 25° C., dark, stored, wrapped in aluminum foil, 4° C.

↓

1 liter starter flasks containing 500 ml starter medium incubated at room temperature, 3 days, on gyratory shaker (300 rpm, 1" radius of gyration)

↓

1.2 v/v inoculum

↓

250 liter fermentor

↓ containing 200 liters culture medium 21° C.; initial aeration rate = 1 vvm, to be adjusted to maintain DO > 50% saturation; agitation rate = 100 rpm Trace metals which can be used in the fermentation broth include magnesium, manganese, zinc, calcium and iron. These metals are added as water soluble salts. Anions such as sulfate, chloride, nitrate and carbonate can be used. The level of copper is very important and should be in the range of from about 10 to about 60 micromoles. Preferably, the amount of copper is from about 45 μm to about 58 μm. The level of trace metals is generally equal to or less than the cupric level.

In addition to the trace metals, a source of nitrogen is required. Ammonium nitrate is the preferred nitrogen source, but other inorganic salts can be used, for example, sodium or potassium nitrate, ammonium sulfate, ammonium hydrogen phosphate, ammonium phosphate, etc. Any alkali metal or alkaline earth metal nitrate can be used. Urea can also be used as a nitrogen source.

The carbon source is preferably glucose or sorbose, but other low molecular weight carbohydrates can be used. These include fructose, sucrose and mannose. The level of carbohydrate is from about 0.2% to about 10% in the fermentation broth.

Thiamine is added at about 1 to about 10 micromoles.

The pH of the medium is held at about 6.0 to about 7.8. The pH is preferably controlled through the use of phosphate buffers, but other buffers can be used.

The temperature of the fermentation is maintained at ambient temperature and preferably between 20° C. and 25° C. If necessary, the level of water is maintained by replacing water lost to evaporation.

During the fermentation reaction, the solution is stirred and aerated with a flow of air. Compressed air which has been filtered to remove any oil or other contaminants is used. For example, the air can be passed through an oil filter and a glass wool plug to remove most of the contaminants. The air flow is adjusted to a rate which maintains the desired degree of oxygen saturation in the broth. Preferably, atmospheric oxygen at above 50% saturation is desirable. Most preferably, the broth is about 75% saturated with oxygen.

The usual length of time that the fermentation is carried out is from about 100 to about 200 hours, preferably from about 120 to about 145 hours.

All of the metal ion solutions, sugar solutions and nitrogen solutions used for preparing the fermentation broth, and any water added during fermentation should be sterilized. This minimizes the formation of interfering enzymes and other fungi, bacteria or viruses.

TABLE 2

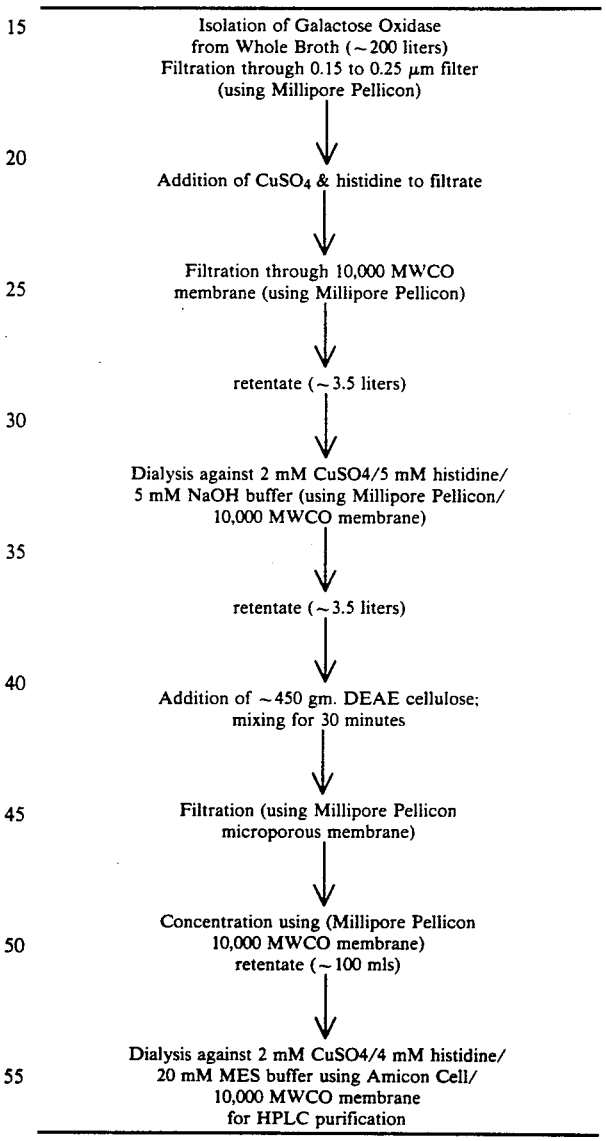

Isolation of Galactose Oxidase from Whole Broth (~200 liters)
Filtration through 0.15 to 0.25 μm filter (using Millipore Pellicon)

↓

Addition of CuSO4 & histidine to filtrate

↓

Filtration through 10,000 MWCO membrane (using Millipore Pellicon)

↓ retentate (~3.5 liters)

↓

Dialysis against 2 mM CuSO4/5 mM histidine/ 5 mM NaOH buffer (using Millipore Pellicon/ 10,000 MWCO membrane)

↓ retentate (~3.5 liters)

↓

Addition of ~450 gm. DEAE cellulose; mixing for 30 minutes

↓

Filtration (using Millipore Pellicon microporous membrane)

↓

Concentration using (Millipore Pellicon 10,000 MWCO membrane) retentate (~100 mls)

↓

Dialysis against 2 mM CuSO4/4 mM histidine/ 20 mM MES buffer using Amicon Cell/ 10,000 MWCO membrane for HPLC purification

B. Isolation of the Galactose Oxidase

Table 2 illustrates the isolation process.

The contents of the fermentation batches are cooled to about 3° to about 10° C. and filtered through a 0.15 to 0.25 μm filter. Conventional filters such as millipore or other filters are acceptable. Use of a millipore filter is a preferable filtration technique because it also removes gel-like polymers which can foul the membrane of the ultrafiltration apparatus in the next step. However, other means of filtration such as nylon mesh sheet CMN-210 (Small Points, Florida) can also be used.

Copper sulfate and histidine are added to the filtrate in the amount necessary to make a 8mM to about a 12 mM solution of copper ion (cupric) and about 15 mM to about 25 mM of histidine.

The filtrate is concentrated to about 10% to about 25% by ultrafiltration through a 10,000 molecular weight cut off membrane: Millipore Pellicon Cassette System can be used as can other ultrafiltration systems.

The retentate is optionally equilibrated with a freshly prepared buffer (pH about 7.0) containing copper sulfate (3-8 mM), histidine (3-8mM) and sodium hydroxide (3-8mM). Again the solution is concentrated to about equal volumes as before.

The retentate is optionally treated with DEAE cellulose which has been equilibrated with a phosphate buffer (pH about 7.0) containing copper sulfate and histidine. The cellulose adsorbs about 50% of the contaminating proteins from the retentate, i.e. the galactose oxidase containing solution. Removal of these proteins facilitates the final purification of the enzymes. The cellulose is filtered and, if cloudy, centrifuged to remove any materials. A 5 minute to about 30 minute cellulose treatment is usually sufficient to remove these proteins.

This solution is again subjected to ultrafiltration to further concentrate it to about 10% to about 25% of the starting solution. The enzyme is equilibrated during this concentration with a solution of copper sulfate (2mM to about 20mM), histidine (4mM to 40mM) and MES (2-(N-morpholino) ethanesulfonic acid) (10 mM to 30mM) at a pH of about 5.6 using a 10,000 molecular weight cut off (MWCO) dialysis bag.

Any cloudiness or fine particles left in the solution can be removed by filtration or centrifugation.

C. Chromatography

The enzyme solution is finally purified using high performance liquid chromatography (HPLC). A carboxy-sulfon 40 micron column from J. T. Baker (Phillipsburg, N.J.) is used. BAKERBOND CARBOXY-SULFON is a trade marked product of J. T. Baker. The carboxy-sulfon columns can contain particles ranging from 5 microns to 50 microns in size. The carboxy-sulfon substrate is described in U.S. Pat. No. 4,721,573 which is incorporated by reference herein. These columns are sulfonic derivatives of N-acylated covalently bound, non-crosslined polyethyleneimine bonded phase silicas of the formula:

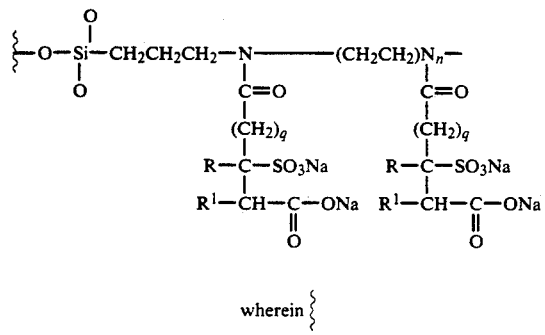

wherein is the backbone of a silica gel or glass, n is an integer such that the polyethyleneiminopropyl silane group has an average molecular weight of from about 400 to about 1800; q is an integer of zero or one; R is selected from the group consisting of hydrogen, gen, $-(CH_2-)_x-H$ or $-(CH_2)_mCOOH$ where x is an integer of 1 or 2 and m is an integer of zero or one; when R is hydrogen or $-(CH_2-)_x-H$ then $R^1$ is $-(CH_2)_pCOOH$ where p is an integer of zero or one, and when R is $-(CH_2)_mCOOH$ then $R^1$ is selected from the group consisting of hydrogen or $-(CH_2)_yH$ where y is an integer, zero or one.

After injection of a crude enzyme solution and elution of a void volume with a buffer composed of MES, histidine and cupric sulfate, a linear gradient is applied of a buffer containing sodium acetate, histidine and cupric sulfate. Usually this elution is done over about 1 to 2 hours with a flow rate of about 5 ml/min. to about 2 ml/min. A step gradient of about 10% to about 15% is generally used.

The exact concentration gradients and times will depend on the solution and the column length as well as the method of loading the column. One skilled in the art will be able to determine the exact method with minimal experimentation. The enzyme position is determined using a ultraviolet light at 280 nm.

D. Assay Methods

An assay solution is prepared by boiling a phosphate buffer (0.1M, pH 7.0) and then cooling it to a room temperature. To this buffer is added 500 mg of D-galactose (available from Sigma as a "substantially glucose free" material), 5 mg horseradish peroxidase, (available from Sigma, type III mixture of basic isozymes) and 5 mg o-dianisidine (3, 3'-dimethoxybenzidine), dissolved in 0.5 ml of methanol. These solutions are added to the phosphate buffer and the buffer is diluted to 100 ml in a volumetric flask. 0-Dianisidine (3-3'-dimethoxybenzidine) should be added quickly otherwise a cloudy suspension will result. The assay solution must be stored away from the light and be refrigerated. The solution should be discarded when the absorbance at 460 nm becomes greater than 0.1 than the buffer solution alone.

To assay the activity of the glactose oxidase, one ml of the assay solution is added at room temperature to a microcuvette for an ultraviolet spectrometer. A sample of the enzyme (5 to 50 microliters) is injected into the assay solution and stired for about a second. The linear absorbance increase is followed for one minute and the absorbance/per minute is calculated. The amount of enzyme added should be adjusted until this value is between 0.2 and 0.6.

When using solid enzyme samples, the solid sample is dissolved in 0.1 M phosphate buffer (pH 7.0) to make the amount of enzyme equal to approximately 0.4 units in the assay mixture.

Protein Assay

Bio-Rad protein assay dye concentrate, catalogue number 500-006 is used for an assay standard. This protein assay dye should be diluted to a concentration of about one (1) volume of concentrate to four (4) volumes of distilled water. A solution of bovine serum albumin in 0.15 M sodium chloride is prepared (1 mg per ml). Ten samples containing from 10 to 100 micrograms of the protein are added to test tubes (10 microliter, 20 microliter, etc.) The volume in each test tube is adjusted to 0.1 milliliter. Five ml of the assay solution is measured into each test tube and mixed for 30 seconds. After 2 minutes, the absorbance at 595 nm against a blank solution prepared from 0.1 ml of 0.15 M sodium chloride in 5 ml of assay solution is measured. The weight of the protein is plotted against the absorbance.

EXAMPLE 1

Fermentation of Galactose Oxidase in 20 L Bottles

*Dactylium Dendroides* strain NRRL 2903 was obtained from Dr. J. J. Ellis of the USDA of the Northern Regional Research Laboratory (Pioria, Ill.) and was maintained on agar slants. A 20 liter autoclaveable plastic bottle was equipped with four metal aerators and a three stage turbine propeller for mixing. Compressed air was filtered through an oil removal filter (DPS-19 from Grainview Products, California) followed by sterile glass wool filters. After passing through the filters, the air is distributed through the four aerators in the bottle. During the fermentation, the total air flow in each bottle (fermentation flask) is maintained at 19 liters/minute as measured at the outlet of the air.

Agar Slants:
  Starter Medium +1.5% agar
Starter Medium:
  5.88 parts Solution A +1 part Solution B +1 part Solution C +0.0006 parts Solution D
Culture Medium:
  8 parts Solution A +1 part Solution C +0.0008 parts Solution D
Solution A: (salts, nitrogen)
  10.74 g/l $Na_2HPO_4$
  10.41 g/l $KH_2PO_4$
  1.27 g/l $(NH_4)_2NO_3$
  2.50 g/l $(NH_4)_2SO_4$
  0.93 g/l NaOH
  1.07 g/l KOH
Solution B: (trace metals)
  2.05 g/l $MgSO_4$
  19.48 mg/l $MnSO_4.H_2O$
  30.00 mg/l $ZnSO_47.H_2O$
  17.75 mg/l $CaCl_22.H_2O$
  28.44 mg/l $FeSO_47.H_2O$
  135 mg/l $CuSO_45.H_2O$
Solution C: (carbon source)
  for agar slants and starter flasks:
    79.4 g/l glucose
  for culture flask/fermentor
    100.- g/l sorbose
Solution D: (thiamine)
  33.7 g/l thiamine, filter-sterilized The fermentation flasks are maintained at 21° C. in water baths. Temperature control is provided by circulating water in the tubing of the cooling or heating medium by a thermostat.

Solution A is placed in the fermentation flask. Stirrers and aerators are then inserted into the flask and a slow flow of air is turned on. Stirring rate is maintained at 490 RPM (gentle stirring). Solutions B and C are added to each flask followed by the addition of a thiamine stock solution (800 microliters). The fermentators are then innoculated with 120 ml of the mycelia suspension from the starter flask. The air flow is adjusted from 19 liters/minute and the fermentation was allowed to continue from 136 to 140 hours.

After 48 hours of fermentation, two liters of sterile water is added to the flask to replace the water which is evaporated.

The broth from the fermentation is filtered through 210 micrometer nylon mesh sheets and the mycelia is squeezed dry. The volume of the filtrate is measured, and copper sulfate and histamine are added to the filtrate in amounts to make a 10 millimolar solution of copper sulfate and a 20 millimoler solution of histamine. The solution is filtered through a GF/D Whatman glass fiber filter and a 0.22 micrometer millipore filter (millidisc hydrophobic cartridge). The solution is fed into the cartridge from a pressurized container. The fine filtration is necessary to remove a gel-like polymer. Two cartridges are used, one for each 15 liters of the solution. The filtered solution is concentration to about 500 ml by ultrafiltration using a millipore Pellicon cassette system equipped with a 10,000 MWCO membrane cassette. This concentration takes from 1-2 hours for the 30 liter solution. The retentate is equilibrated on the same millipore Pellicon cassette system with a freshly prepared buffer containing copper sulfate, (5 millimoles), histidine (5 millimoles) and sodium hydroxide (5 millimoles), a pH of about 5.6.

The retentate is treated with DEAE cellulose (60 grams) equilibrated with the same buffer as was used in the ultrafiltration system and stirred for 15 minutes. The cellulose is removed by suction filtration. The filtrate is centrifuged at 9,000 g for 30 minutes to remove any cloudiness or precipitation.

The clear enzyme solution is concentrated to about 15 ml using an Amicon stirred ultrafiltration cell equipped with 10,000 MWCO membrane (PM-10 diameter 76 mm) at 40 psi. This ultrafiltration takes 3-6 hours. The concentrated enzyme solution is equilibrated with a solution of copper sulfate (2 millimoles), histidine (4 millimoles), and MES (20 millimoles) at a pH of 5.6 using a dialysis bag fitted with a 10,000 MWCO membrane size. The retentate is centrifuged at 9,000 g for 30 minutes to remove any cloudiness. The concentrate is filtered through a plug of G/F Whatman glass fiber filter to remove fine particles from this solution.

A high performance liquid chromatography column is filled with 40 microns carboxy-sulfon (J. T. Baker, BAKERBOND CARBOXY-SULFON) (40.6×250 mm). The concentrated enzyme solution (1.75 ml) is loaded onto the column using a 2 ml loop. The void volume peak is eluted and collected. Four to five portions of the concentrated crude enzyme are injected onto the column and the void volumes eluted. After the last void volume is eluted, a linear gradient from 100% A to 100% B over a one hour period is applied. The flow rate is 1 ml per minute. Buffer A is a mixture of 20 mM 2-N morpholino ethane sulfonic acid (MES), 2 millimolar copper sulfate, 4 millimolar histidine at a pH of 5.6 adjusted with sodium hydroxide. Buffer B is a 1 molar solution of sodium acetate, 2 millimolar copper sulfate, 4 millimolar histidine at a pH of 5.8 adjusted with acetic acid or sodium hydroxide. The galactose oxidase enzyme elutes in about 16 minutes. An ultraviolet detector set at 280 nm can be used to detect the enzyme.

Void volumes are analyzed for the presence of galactose oxidase by standard activity analysis. If enzyme is present, the void solution can be rechromatographed after concentration by ultrafiltration) in the presence of copper ions and histidine.

A yield of 70% galactose oxidase is obtained.

What is claimed is:

1. A process for preparing galactose oxidase enzyme solutions comprising the steps of:
   (1) aerobically fermenting a *Dactylium dendroides* source of galactose oxidase in a medium comprising a nitrogen source, a carbon source, trace metals, thiamine and from 10 to about 60 micromolar in copper at a temperature of between 20° C. to about 25° C.;

(2) filtering the supernatant liquid from the fermentation broth using a 0.15 to 0.25 μm filter;

(3) concentrating the enzyme by ultrafiltration with a 10,000 molecular weight membrane;

(4) equilibrating the retentate from (3) with a buffer containing copper ions, histidine and hydroxide ion; and (5) purifying the enzyme using high performance liquid chromatography methods on a carboxy-sulfon column wherein said column comprises sulfonic derivatives of N-acylated covalently bound, non-crosslined polyethyleneimine bonded phase silicas wherein the enzyme is eluted with a buffer having a pH of 5.8 comprising histidine, sodium acetate and cupric ions.

2. A process according to claim 1 wherein the carboxy-sulfon column has particles ranging from 5 microns to 50 microns in size.

3. A process according to claim 2 wherein the enzyme is eluted at a flow rate of 0.5 to about 2 ml/min.

4. A process according to claim 3 in which the retentate from step (4) is treated with DEAE cellulos to remove contaminating proteins.

5. A process according to claim 3 wherein said carboxysulfon has the formula:

$$\xi-O-\underset{\underset{O}{|}}{\overset{\overset{O}{\|}}{Si}}-CH_2CH_2CH_2-\underset{\underset{\underset{\underset{R^1-CH-C-ONa}{\overset{\|}{O}}}{\overset{|}{R-C-SO_3Na}}}{\overset{|}{C=O}}}{\overset{|}{N}}-(CH_2CH_2)N_n-\underset{\underset{\underset{R^1-CH-C-ONa}{\overset{\|}{O}}}{\overset{|}{R-C-SO_3Na}}}{\overset{|}{C=O}}$$

wherein ξ is the backbone of a silica gel or glass, n is an integer such that the polyethyleneiminopropyl silane group has an average molecular weight of from about 400 to about 1800; q is an integer of zero or one; R is selected from the group consisting of hydrogen, gen —(CH$_2$—)$_x$—H or —(CH$_2$)$_m$COOH where x is an integer of 1 or 2 and m is an integer of zero or one; when R is hydrogen or —(CH$_2$—)$_x$—H then R$^1$ is —(CH$_2$)$_p$COOH where p is an integer of zero or one, and when R is —(CH$_2$)$_m$COOH then R$^1$ is selected from the group consisting of hydrogen or —(CH$_2$)$_y$H where y is a integer of zero or 1.

6. A process according to claim 5 wherein said carbon source is glucose or sorbose.

7. A process according to claim 6 wherein said filter in step (2) is a 0.22 μm millipore filter.

8. A process according to claim 7 wherein said nitrogen source is selected from the group consisting of nitrate salts of alkali and alkaline earth metals and ammonium salts.

9. A process according to claim 8 wherein said nitrogen source is selected from the group of ammonium nitrate, ammonium sulfate and mixtures thereof.

10. A process according to claim 9 wherein said trace metals comprise a mixture of copper, calcium, magnesium, iron, manganese and zinc ions.

11. A process according to claim 9 wherein the pH of the fermentation reaction is about 6.0 to about 7.8.

12. A process according to claim 11 wherein said buffer in step (4) has a pH of about 5.6.

* * * * *